(12) United States Patent
Mizori

(10) Patent No.: US 7,884,174 B2
(45) Date of Patent: Feb. 8, 2011

(54) IMIDE-LINKED MALEIMIDE AND POLYMALEIMIDE COMPOUNDS

(75) Inventor: Farhad G. Mizori, La Mesa, CA (US)

(73) Assignee: Designer Molecules, Inc., San Diego, CA (US)

( * ) Notice: Subject to any disclaimer, the term of this patent is extended or adjusted under 35 U.S.C. 154(b) by 884 days.

(21) Appl. No.: 11/786,029

(22) Filed: Apr. 11, 2007

(65) Prior Publication Data

US 2008/0075961 A1 Mar. 27, 2008

Related U.S. Application Data

(60) Continuation-in-part of application No. 11/642,995, filed on Dec. 19, 2006, now abandoned, which is a division of application No. 10/835,911, filed on Apr. 30, 2004, now Pat. No. 7,208,566.

(60) Provisional application No. 60/468,037, filed on May 5, 2003.

(51) Int. Cl.
*C08G 69/08* (2006.01)
*C08G 73/10* (2006.01)
*C08G 73/14* (2006.01)

(52) U.S. Cl. .................. 528/310; 528/322; 526/262; 525/282; 525/202; 525/322; 524/439

(58) Field of Classification Search ............... 528/310, 528/322; 526/262; 525/282, 202, 322; 524/439
See application file for complete search history.

(56) References Cited

U.S. PATENT DOCUMENTS

| | | | |
|---|---|---|---|
| 5,284,959 A | 2/1994 | Marien et al. |
| 5,393,887 A | 2/1995 | Petit |
| 5,554,769 A | 9/1996 | Sheppard et al. |
| 5,760,165 A | 6/1998 | Dao et al. |
| 5,973,166 A | 10/1999 | Mizori et al. |
| 6,034,194 A | 3/2000 | Dershem |
| 6,034,195 A | 3/2000 | Dershem |
| 6,063,828 A | 5/2000 | Ma |
| 6,187,886 B1 | 2/2001 | Husson et al. |
| 6,265,530 B1 | 7/2001 | Herr |
| 6,281,314 B1 | 8/2001 | Tong |
| 6,316,566 B1 | 11/2001 | Ma |
| 6,355,750 B1 | 3/2002 | Herr |
| 6,699,929 B2 | 3/2004 | Musa |
| 6,790,597 B2 | 9/2004 | Dershem |
| 6,825,245 B2 | 11/2004 | Dershem |
| 6,831,132 B2 | 12/2004 | Liu et al. |
| 6,852,814 B2 | 2/2005 | Dershem |
| 6,916,856 B2 | 7/2005 | Dershem |
| 7,208,566 B2 | 4/2007 | Mizori et al. |

OTHER PUBLICATIONS

International Search Report for WO 2004/099331 A3, Jul. 14, 2005.

*Primary Examiner*—Duc Truong
(74) *Attorney, Agent, or Firm*—The Law Office of Jane K. Babin, Professional Corporation; Jane K. Babin

(57) ABSTRACT

The invention is based on the discovery that a remarkable improvement in the performance of maleimide thermosets can be achieved through the incorporation of imide-extended mono-, bis-, or polymaleimide compounds. These imide-extended maleimide compounds are readily prepared by the condensation of appropriate anhydrides with appropriate diamines to give amine terminated compounds. These compounds are then condensed with excess maleic anhydride to yield imide-extended maleimide compounds.

21 Claims, 3 Drawing Sheets

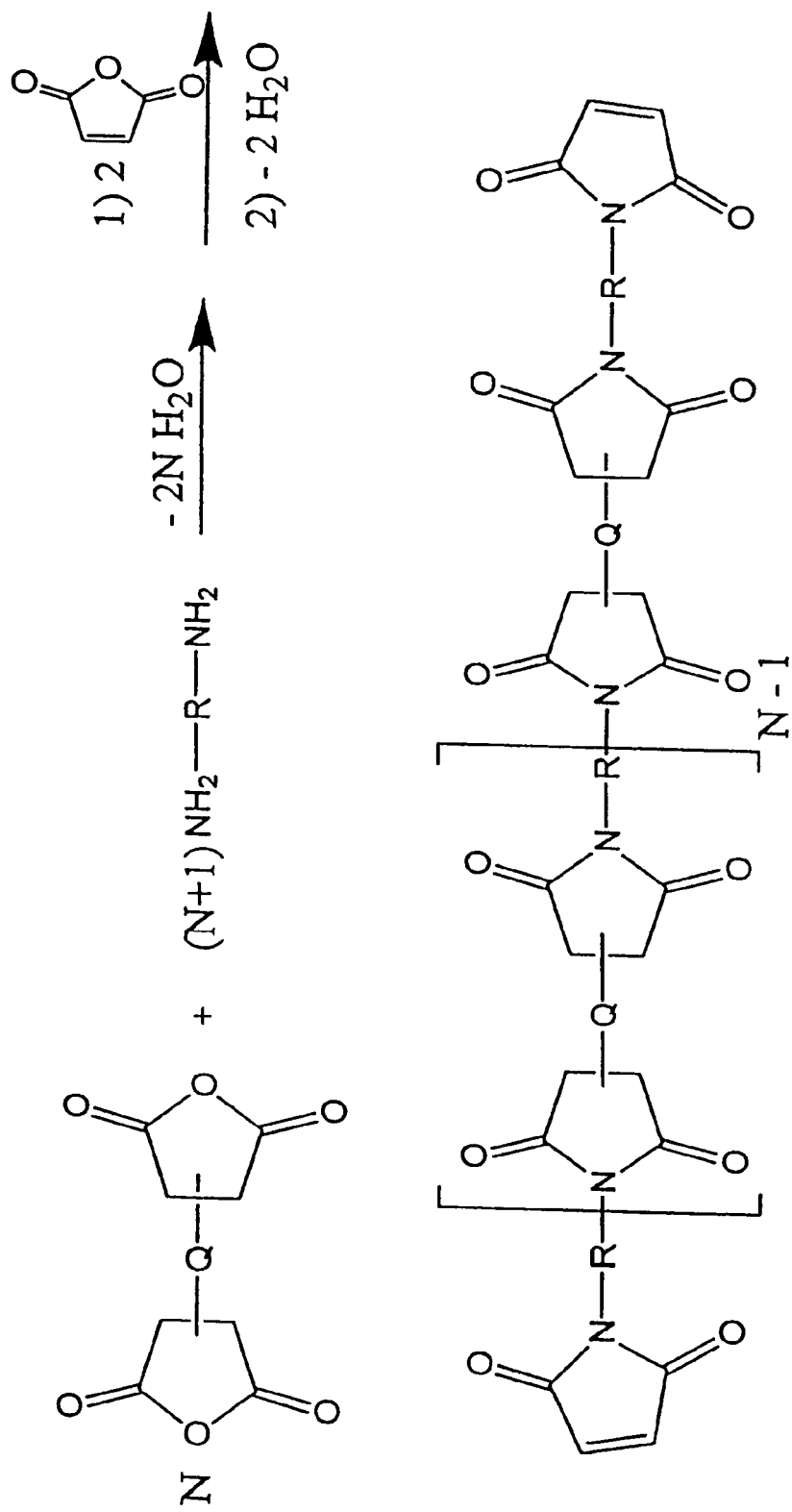
Figure 1. Generic Preparation of a Maleimide End-capped Polyimide

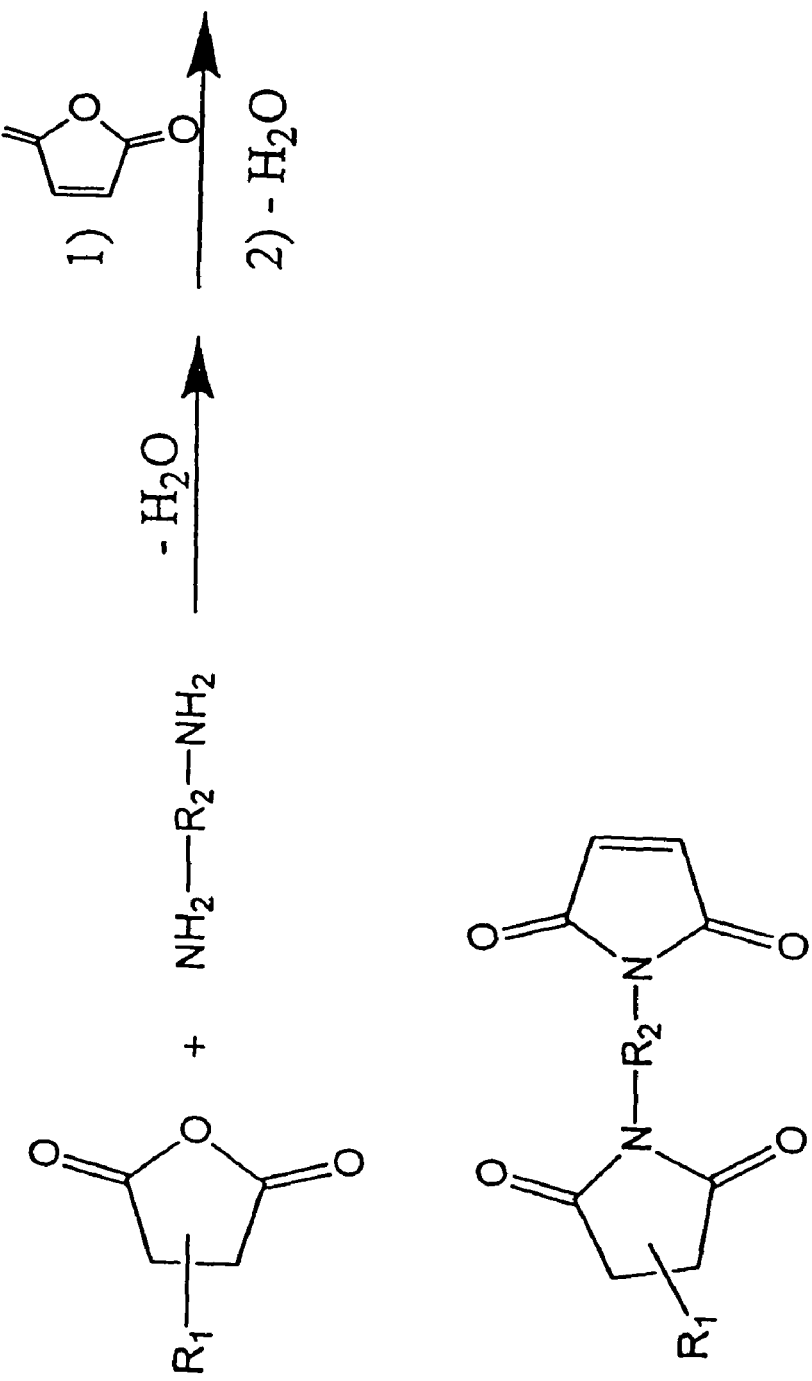
Figure 2. Generic Preparation of an imide-bridged Monomaleimide

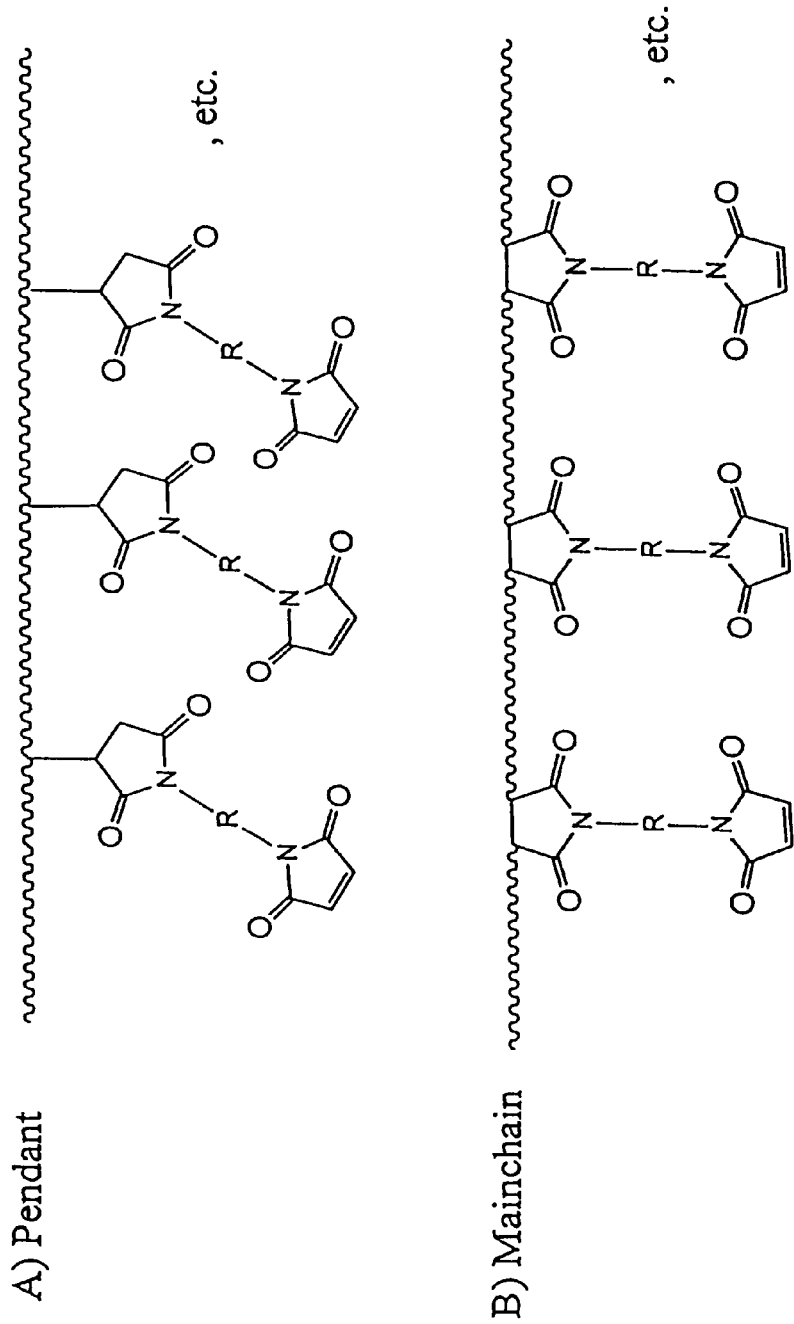
Figure 3. Generic Multi-maleimide-functional imide-bridged Polymers
A) Pendant
B) Mainchain

IMIDE-LINKED MALEIMIDE AND POLYMALEIMIDE COMPOUNDS

RELATED APPLICATION DATA

This application is a continuation-in-part of application Ser. No. 11/642,995, filed Dec. 19, 2006, now abandoned which in turn is a divisional of application Ser. No. 10/835,911, filed Apr. 30, 2004, now U.S. Pat. No. 7,208,566 which claims priority to Application Ser. No. 60/468,037, filed May 5, 2003, the entire contents of each of which are incorporated herein by reference.

FIELD OF THE INVENTION

The present invention relates to thermosetting adhesive compositions methods of preparation and uses therefor. In particular, the present invention relates to thermosetting compounds and compositions containing imide-extended mono-, bis-, and polymaleimide compounds.

BACKGROUND OF THE INVENTION

Adhesive compositions, particularly conductive adhesives, are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards. Adhesives useful for electronic packaging applications typically exhibit properties such as good mechanical strength, curing properties that do not affect the component or the carrier, and thixotropic properties compatible with application to microelectronic and semiconductor components.

The bismaleimides represent one useful class of thermoset compounds that have been used in the microelectronic packaging industry. Bismaleimides are curable, meaning that they are capable of polymerization to yield cross-linked resins. In addition, bismaleimides may be homocured in the presence of free radicals or photoinitiators, or combined with other free-radical curing monomers (e.g., acrylates, methacrylates, syrenics, vinyl ethers, vinyl esters, allyl monomers, olefins, and the like). They may also be cured in the presence of comonomers via, Diels-Alder, -ene, and Michael addition mechanisms.

Commercially available bismaleimide thermoset compositions are noted for their high modulus, and excellent resistance to thermal degradation. However, these thermoset compositions are also well known for brittleness. The utility of the bismaleimide class of thermosets could be vastly improved if less brittle formulations could be achieved that retain the desirable thermal and elastic properties.

SUMMARY OF THE INVENTION

The invention is based on the discovery that a remarkable improvement in the performance of maleimide thermosets can be achieved through the incorporation of an imide-extended mono-, bis-, or polymaleimide compounds. These imide-extended maleimide compounds are readily prepared by the condensation of appropriate anhydrides with appropriate diamines to give amine terminated compounds. These compounds are then condensed with excess maleic anhydride to yield imide-extended maleimide compounds.

When incorporated into a thermoset composition, the imide-extended maleimide compounds described herein reduce brittleness and increase toughness in the composition, while not sacrificing thermal stability. The imide functional group is one of the most thermally stable groups known. Thus, the present invention provides a maleimide functionalized thermoset composition without thermally labile linkages, thereby providing superior thermal stability when used as a toughener.

In one embodiment, there are provided imide-extended bismaleimide compounds having the structure:

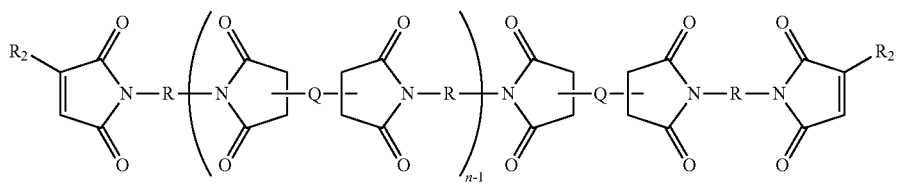

wherein:
R and Q are each independently substituted or unsubstituted aliphatic or alkenyl, aromatic, heteroaromatic, or siloxane moieties;
$R_2$ is H or methyl;
and n is 1 to about 10, with the proviso that the imide-extended bismaleimide is not

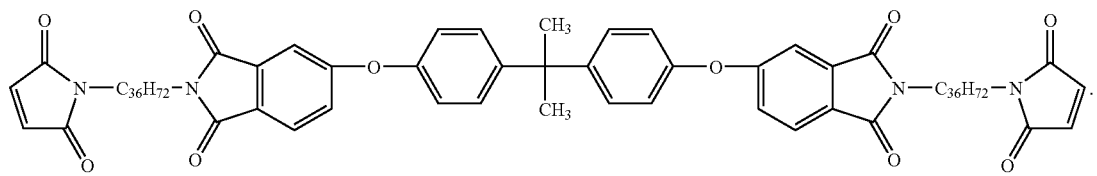

In another embodiment, there are provided monomaleimides having the structure:

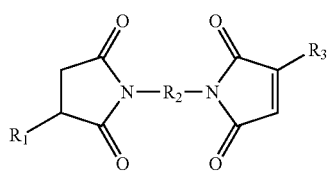

wherein: $R_1$ is substituted or unsubstituted aliphatic, alkenyl, or aromatic; and $R_2$ is substituted or unsubstituted aliphatic, aromatic, or siloxane.

$R_3$ is H or methyl

In still another embodiment, there are provided polymaleimides including polymers including a plurality of pendant repeating units having the structure:

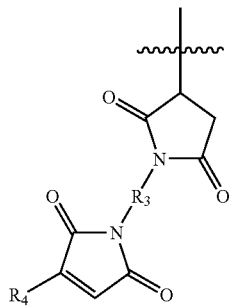

wherein: $R_3$ is substituted or unsubstituted aliphatic, alkenyl, aromatic, heteroaromatic, or siloxane moieties;

$R_4$ is H or methyl

In further embodiments, there are provided polymaleimides including polymers including a plurality of repeating units having the structure:

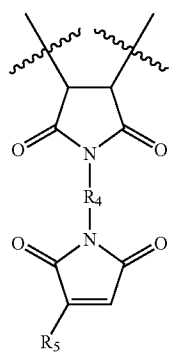

wherein: $R_4$ is a substituted or unsubstituted linear, branched, cyclic aliphatic, or alkenyl moiety having from 2 to about 500 carbon atoms, or a substituted or unsubstituted aromatic moiety; $R_5$ is H or methyl.

In another embodiment, there are provided compounds having the structure:

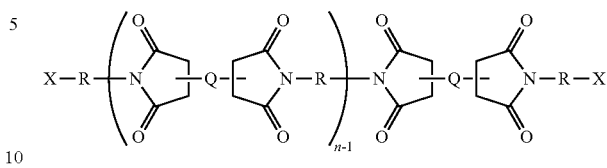

wherein:
R and Q are each independently substituted or unsubstituted aliphatic or alkenyl, aromatic, heteroaromatic, or siloxane moieties; and
X is a polymerizable moiety.

In another embodiment, there are provided adhesive compositions including at least one of the above described monomaleimide, bismaleimide, or polymaleimide compounds, and at least one curing initiator.

In yet another embodiment, there are provided die-attach pastes including
a) 0.5 weight percent to about 98 weight percent (wt %) of at least one of the above described monomaleimide, bismaleimide, or polymaleimide compounds, or combinations thereof, based on total weight of the composition,
b) 0 to about 90 wt % of a filler;
d) 0.1 wt % to about 5 wt % of at least one curing initiator, based on total weight of the composition;
e) 0.1 wt % to about 4 wt %, of at least one coupling agent, based on total weight of the composition.

In a further embodiment, there are provided methods for producing an imide-extended bismaleimide compound. Such methods can be performed, for example, by contacting a dianhydride with a diamine under conditions suitable to form an imide having terminal amino moieties; and contacting the terminal amino moieties with maleic anhydride under conditions suitable to form a maleimide, thereby producing an imide-extended bismaleimide monomer.

In another embodiment, there are provided assemblies including a first article permanently adhered to a second article by a cured aliquot of the die-attach paste according to the invention.

In yet another embodiment, there are provided kits for bonding an electronic component to a substrate comprising a package containing an amount of an adhesive composition comprising an imide-extended mono-, bis-, or polymaleimide sufficient to bond at least one electronic component to a substrate; and instructions for using the adhesive composition to bond the electronic component to the substrate.

In another embodiment, there are provided methods for producing a curable adhesive rope. Such a method can be performed, for example, by
a. providing an adhesive composition comprising an imide-extended mono-, bis- or polymaleimide; and
b. extruding the adhesive composition through a circular shaped form, thereby forming an adhesive rope.

BRIEF DESCRIPTION OF THE DRAWINGS

FIGS. 1 and 2 illustrate an exemplary preparation of an imide-extended compound of the invention.

FIG. 3 shows the generic structure of exemplary polymaleimides of the invention. FIG. 3A shows a polymaleimide structure with succinimide connecting groups pendant from the maleimide polymer or oligomer. FIG. 3B shows a polymaleimide structure where the succinimide connecting groups are part of the main-chain maleimide polymer or oligomer.

DETAILED DESCRIPTION OF THE INVENTION

The present invention is based on the discovery that a remarkable improvement in the performance of maleimide thermosets can be achieved through the incorporation of imide-extended mono-, bis-, or polymaleimide compounds. In one embodiment, there are provided imide-extended bismaleimide compounds having the structure:

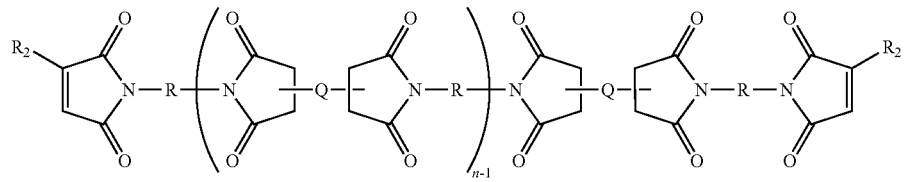

wherein:
R and Q are each independently substituted or unsubstituted aliphatic or alkenyl, aromatic, heteroaromatic, or siloxane moieties;
$R_2$ is H or methyl; and
n is 1 to about 10, with the proviso that the imide-extended bismaleimide is not

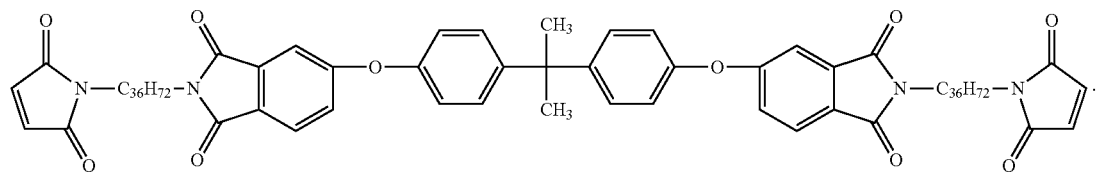

As used herein, the term "imide-extended" means that the compound contains at least one imide moiety in a non-terminal position of the molecule.

As used herein, "cycloalkyl" refers to cyclic ring-containing groups containing in the range of about 3 up to 20 carbon atoms, and "substituted cycloalkyl" refers to cycloalkyl groups further bearing one or more substituents as set forth above.

As used herein, "alkyl" refers to straight or branched chain hydrocarbyl groups.

As used herein, "alkenyl" refers to straight or branched chain hydrocarbyl groups having at least one carbon-carbon double bond, and having in the range of about 2 up to 500 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 500 carbon atoms, and "substituted alkynyl" refers to alkynyl groups further bearing one or more substituents as set forth above.

As used herein, "aryl" refers to aromatic groups having in the range of 6 up to 20 carbon atoms and "substituted aryl" refers to aryl groups further bearing one or more substituents as set forth above.

As used herein, "alkylaryl" refers to alkyl-substituted aryl groups and "substituted alkylaryl" refers to alkylaryl groups further bearing one or more substituents as set forth above.

As used herein, "arylalkyl" refers to aryl-substituted alkyl groups and "substituted arylalkyl" refers to arylalkyl groups further bearing one or more substituents as set forth above.

As used herein, "arylalkenyl" refers to aryl-substituted alkenyl groups and "substituted arylalkenyl" refers to arylalkenyl groups further bearing one or more substituents as set forth above.

As used herein, "arylalkynyl" refers to aryl-substituted alkynyl groups and "substituted arylalkynyl" refers to arylalkynyl groups further bearing one or more substituents as set forth above.

As used herein, "aroyl" refers to aryl-carbonyl species such as benzoyl and "substituted aroyl" refers to aroyl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 20 carbon atoms and "substituted heterocyclic" refers to heterocyclic groups further bearing one or more substituents as set forth above.

As used herein, "acyl" refers to alkyl-carbonyl species.

As used herein, "halogen" refers to fluoride, chloride, bromide or iodide atoms.

In certain embodiments, R and Q are each independently substituted or unsubstituted linear, branched, or cyclic aliphatic or alkenyl moieties having from 2 to about 500 carbon atoms. In other embodiments, R and Q are each independently substituted or unsubstituted aromatic or heteroaromatic moieties having from 6 to about 20 carbon atoms.

In other embodiments, R and Q are each independently substituted or unsubstituted siloxane moieties having from 2 to about 1000 silicon atoms. In some embodiments, R and Q are each independently polysiloxane moieties, such as, for example, dimethylsiloxane, methylphenylsiloxane, diphenylsiloxane, methylhydrosiloxane, or combinations thereof.

When R and Q include substituted aliphatic, aromatic, heteroaromatic, or siloxane moieties, such substituents include alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —S—, —S(O)$_2$—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, sulfuryl, and the like.

In another embodiment, there are provided compounds having the structure:

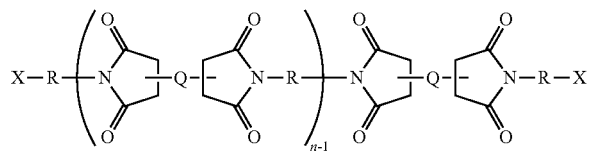

wherein:
R and Q are each independently substituted or unsubstituted aliphatic, aromatic, heteroaromatic, siloxane, unsaturated hydrocarbon, polyester, polyamide, or polyurethane moieties; and
X is a polymerizable or curative moiety.

In some embodiments, the polymerizable moiety is a cationic polymerizable moiety, an anionic polymerizable moiety, a ring-opening polymerizable moiety, or a free radical polymerizable moiety. In some embodiments, the polymerizable moiety is vinyl ether, vinyl ester, acrylate, methacrylate, epoxy, oxetane, oxazoline, benzoxazine, prorpargyl ether, vinyl chloride, urethane, norbornyl maleimide, or nadimide. In some embodiments the curative is phenol, phenyl ester and the like.

Referring to FIG. 1, imide-extended bismaleimide compounds are readily prepared by a two-step, single-pot synthesis. The first step involves the condensation of a dianhydride with a dimer diamine to form an amine-terminated polyimide. The diamine should be present in at least a slight excess of that necessary to form the imide-linked diamine intermediate.

A wide variety of diamines are contemplated for use in the practice of the invention, such as for example, 1,10-diaminodecane; 1,12-diaminododecane; dimer diamine; 1,2-diamino-2-methylpropane; 1,2-diaminocyclohexane; 1,2-diaminopropane; 1,3-diaminopropane; 1,4-diaminobutane; 1,5-diaminopentane; 1,7-diaminoheptane; 1,8-diaminomenthane; 1,8-diaminooctane; 1,9-diaminononane; 3,3'-diamino-N-methyldipropylamine; diaminomaleonitrile; 1,3-diaminopentane; 9,10-diaminophenanthrene; 4,4'-diaminooctafluorobiphenyl; 3,5-diaminobenzoic acid; 3,7-diamino-2-methoxyfluorene; 4,4'-diaminobenzophenone; 3,4-diaminobenzophenone; 3,4-diaminotoluene; 2,6-diaminoanthroquinone; 2,6-diaminotoluene; 2,3-diaminotoluene; 1,8-diaminonaphthalene; 2,4-diaminotoluene; 2,5-diaminotoluene; 1,4-diaminoanthroquinone; 1,5-diaminoanthroquinone; 1,5-diaminonaphthalene; 1,2-diaminoanthroquinone; 2,4-cumenediamine; 1,3-bisaminomethylbenzene; 1,3-bisaminomethylcyclohexane; 2-chloro-1,4-diaminobenzene; 1,4-diamino-2,5-dichlorobenzne; 1,4-diamino-2,5-dimethylbenzene; 4,4'-diamino-2,2'-bistrifluoromethylbiphenyl; bis(amino-3-chlorophenyl)ethane; bis(4-amino-3,5-dimethylphenyl)methane; bis(4-amino-3,5-diethylphenyl)methane; bis(4-amino-3-ethyl diaminofluorene; diaminobenzoic acid; 2,3-diaminonaphthalene; 2,3-diaminophenol; -5-methylphenyl)methane; bis(4-amino-3-methylphenyl)methane; bis(4-amino-3-ethylphenyl)methane; 4,4'-diaminophenylsulfone; 3,3'-diaminophenylsulfone; 2,2-bis(4, -(4-aminophenoxy)phenyl)sulfone; 2,2-bis(4-(3-aminophenoxy)phenyl)sulfone; 4,4'-oxydianiline; 4,4'-diaminodiphenyl sulfide; 3,4'-oxydianiline; 2,2-bis(4-(4-aminophenoxy)phenyl)propane; 1,3-bis(4-aminophenoxy)benzene; 4,4'-bis(4-aminophenoxy)biphenyl; 4,4'-diamino-3,3'-dihydroxybiphenyl; 4,4'-diamino-3,3'-dimethylbiphenyl; 4,4'-diamino-3,3'-dimethoxybiphenyl; Bisaniline M; Bisaniline P; 9,9-bis(4-aminophenyl)fluorene; o-tolidine sulfone; methylene bis(anthranilic acid); 1,3-bis(4-aminophenoxy)-2,2-dimethylpropane; 1,3-bis(4-aminophenoxy)propane; 1,4-bis(4-aminophenoxy)butane; 1,5-bis(4-aminophenoxy)butane; 2,3,5,6-tetramethyl-1,4-phenylenediamine; 3,3',5,5'-tetramehylbenzidine; 4,4'-diaminobenzanilide; 2,2-bis(4-aminophenyl)hexafluoropropane; polyoxyalkylenediamines (e.g. Huntsman's Jeffamine D-230, D400, D-2000, and D-4000 products); 1,3-cyclohexanebis(methylamine); m-xylylenediamine; p-xylylenediamine; bis(4-amino-3-methylcyclohexyl)methane; 1,2-bis(2-aminoethoxy)ethane; 3(4),8(9)-bis(aminomethyl)tricyclo(5.2.1.0$^{2,6}$)decane; and the like.

The second step of the reaction involves the condensation of the remaining amine residues with a slight excess of maleic anhydride to form the maleimide moieties. This second step can be accomplished employing techniques well known to those of skill in the art. The most straightforward preparation of maleimides entails formation of the maleamic acid via reaction of the primary amine with maleic anhydride, followed by dehydrative closure of the maleamic acid with acetic anhydride. A major complication is that some or all of the closure is not to the maleimide, but to the isomaleimide. Essentially the isomaleimide is the dominant or even exclusive kinetic product, whereas the desired maleimide is the thermodynamic product. Conversion of the isomaleimide to the maleimide is effectively the slow step and, particularly in the case of aliphatic amines, may require forcing conditions which can lower the yield. Of course, a variety of other approaches can also be employed.

For example, dicyclohexylcarbodiimide (DCC) closes maleamic acids much more readily than does acetic anhydride. With DCC, the product is exclusively isomaleimide. However, in the presence of suitable isomerizing agents, such as 1-hydroxybenzotriazole (HOBt), the product is solely the maleimide. The function of the HOBt could be to allow the closure to proceed via the HOBt ester of the maleamic acid (formed via the agency of DCC) which presumably closes preferentially to the maleimide. Likely, isomerizing agents such as HOBt add to the isoimide to yield the amic acid ester. If this exhibits any tendency whatsoever to close to the imide, much less a strong bias for doing so, a route for interconverting isoimide and imide is thereby established and the thermodynamic product, imide, should ultimately prevail. Thus if the initial closure of ester formed in the DCC reaction yields any isoimide, or if any isoimide is produced by direct closure of the acid, the situation will be subsequently "corrected" via conversion of the isoimide to the imide by the action of the active ester alcohol as an isomerizing agent. An alternative method for affecting the cyclodehydration of maleamic acids is set forth in U.S. Pat. No. 5,973,166, the entire contents of which are incorporated herein by reference. This method utilizes amine salts that can be successfully used to replace the polar, aprotic solvents that have been used for the cyclodehydration of maleamic acids. The use of these salts provides competitive reaction times and product yields relative to results obtained with polar, aprotic solvents. These salts have the advantage of having no vapor pressure and, therefore, have no possibility to co-distill with the water produced by the cyclodehydration reaction. Furthermore, such salts can be tailored to have desirable solubility characteristics (i.e., soluble in the refluxing azeotropic solvent, but insoluble at room temperature) that permit their easy removal from the reaction product. Such salts are not destroyed during the cyclodehydration reaction and, therefore, can be efficiently recycled again and again.

A wide variety of anhydrides are contemplated for use in the practice of the invention, such as, for example, polybutadiene-graft-maleic anhydride; polyethylene-graft-maleic anhydride; polyethylene-alt-maleic anhydride; polymaleic anhydride-alt-1-octadecene; polypropylene-graft-maleic anhydride; poly(styrene-co-maleic anhydride); pyromellitic dianhydride; maleic anhydride, succinic anhydride; 1,2,3,4-cyclobutanetetracarboxylic dianhydride; 1,4,5,8-naphthalenetetracarboxylic dianhydride; 3,4,9,10-perylenentetracarboxylic dianhydride; bicyclo(2.2.2)oct-7-ene-2,3,5,6-tetracarboxylic dianhydride; diethylenetriaminepentaacetic dianhydride; ethylenediaminetetraacetic dianhydride; 3,3',4,4'-benzophenone tetracarboxylic dianhydride; 3,3',4,4'-biphenyl tetracarboxylic dianhydride; 4,4'-oxydiphthalic anhydride; 3,3',4,4'-diphenylsulfone tetracarboxylic dianhydride; 2,2'-bis(3,4-dicarboxyphenyl)hexafluoropropane dianhydride; 4,4'-bisphenol A diphthalic anhydride; 5-(2,5-dioxytetrahydro)-3-methyl-3-cyclohexene-1,2-dicarboxylic anhydride; ethylene glycol bis(trimellitic anhydride); hydroquinone diphthalic anhydride; allyl nadic anhydride; 2-octen-1-ylsuccinic anhydride; phthalic anhydride; 1,2,3,6-tetrahydrophthalic anhydride; 3,4,5,6-tetrahydrophthalic anhydride; 1,8-naphthalic anhydride; glutaric anhydride; dodecenylsuccinic anhydride; hexadecenylsuccinic anhydride; hexahydrophthalic anhydride; methylhexahydrophthalic anhydride; tetradecenylsuccinic anhydride; and the like.

Additional anhydrides contemplated for use include, but are not limited to,

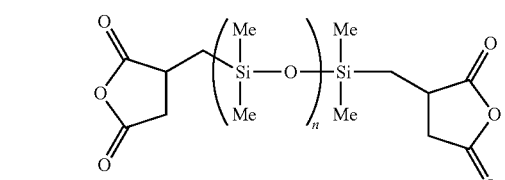

n = 1-1000

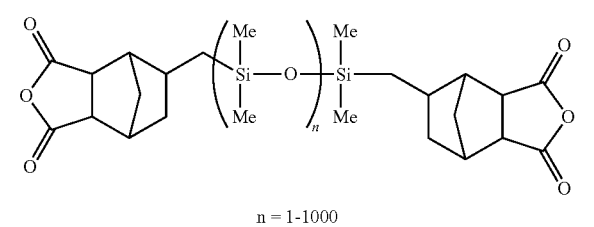

n = 1-1000

-continued

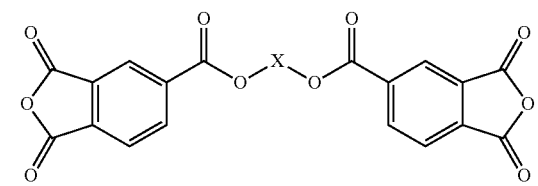

n = 1-1000

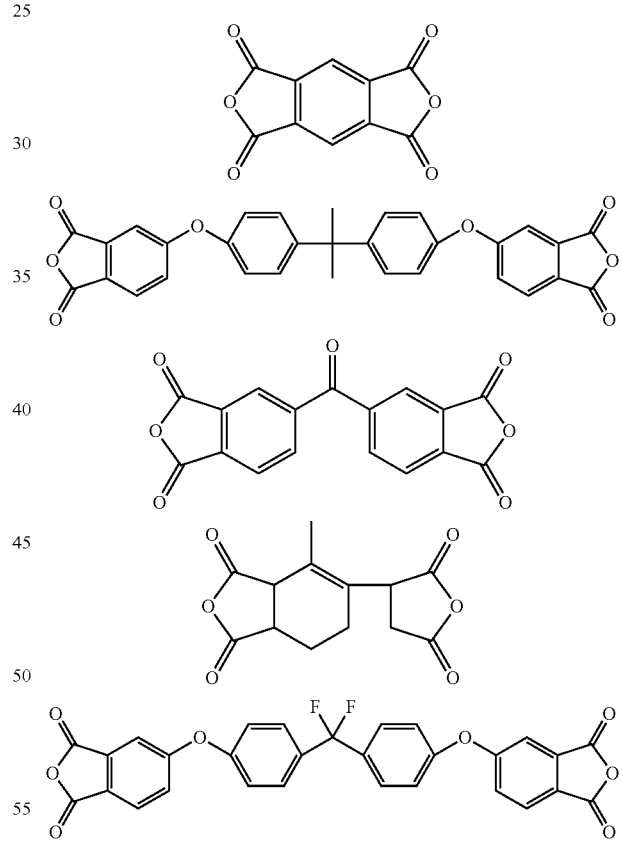

Where X=saturated or unsaturated strait or branched alkyl
  X=Polyester, polyamide, polyether, polysiloxane, polyurethane

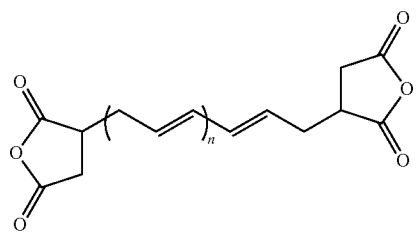

n = 1-10

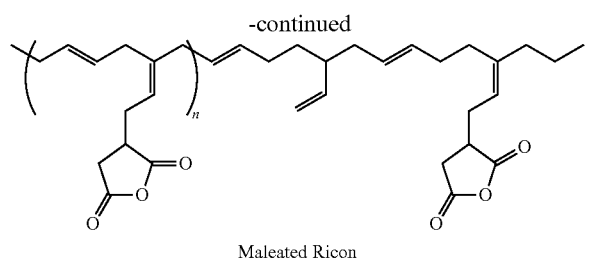
Maleated Ricon
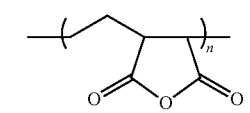
Polyethylene-graft-Maleic anhydride
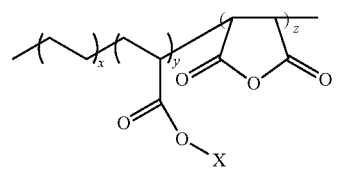
Polyethylene-alt-maleic anhydride
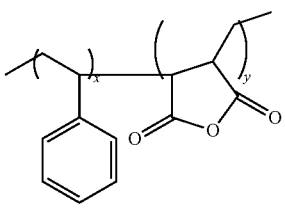
Poly(ethylene-co-x-acrylate-co-maleic anhydride)
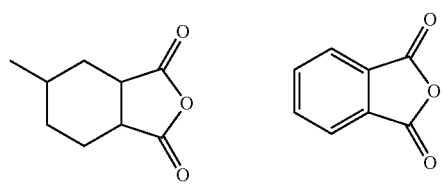
Poly(styrene-co-maleic anhydride)
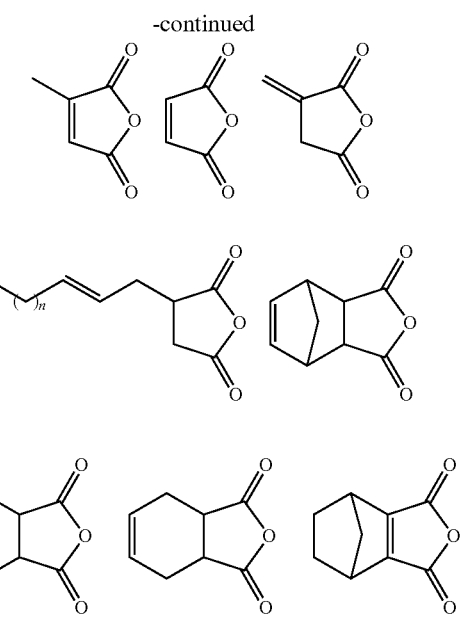
All of the following compounds are also contemplated for use in the practice of the invention:
Maleimides, Citraconimides, and Itaconimides
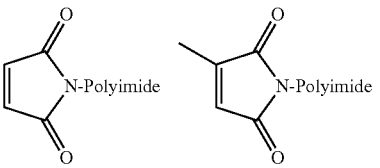
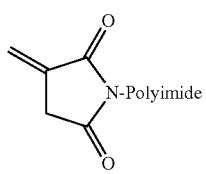
Other Alkene End Groups
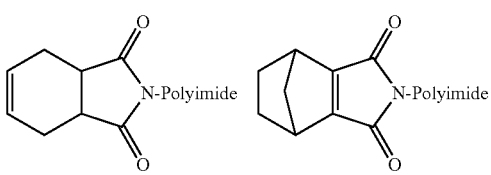
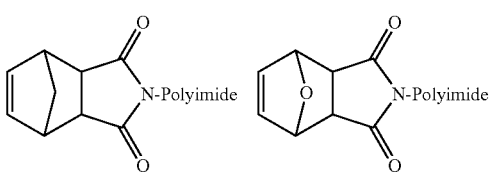

Cycloaliphatic Epoxies
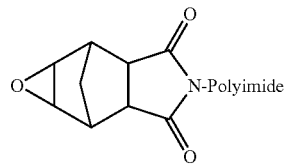 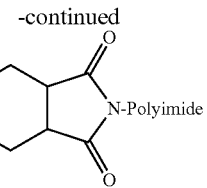
Amines, Alcohols, Carboxylic acids, Phenols, thiols.
H—O-Polyimide    H—S-Polyimide    H₂N-Polyimide    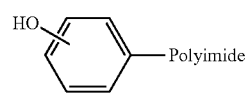 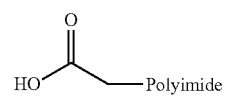
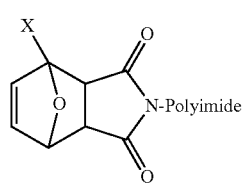 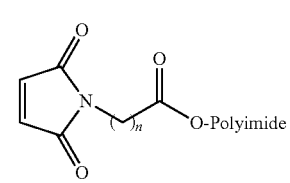 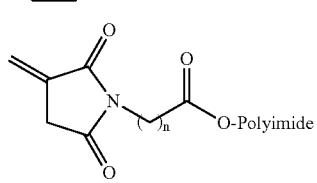 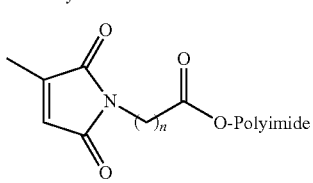
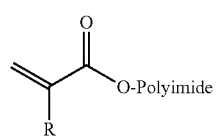 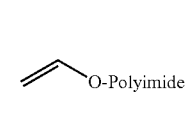 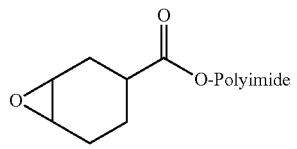 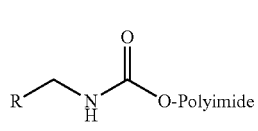
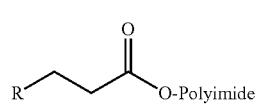 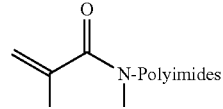 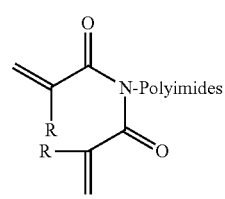 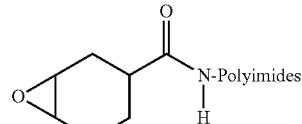
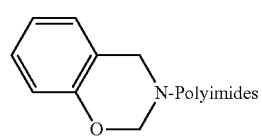 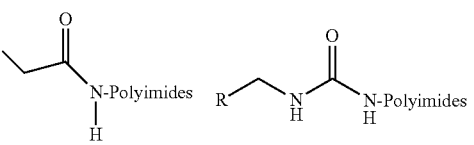 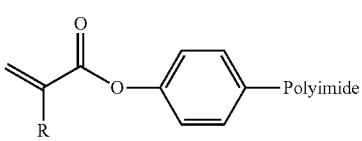
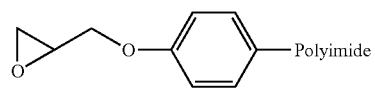 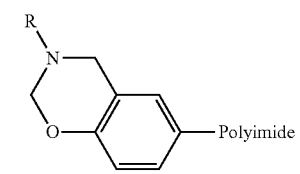 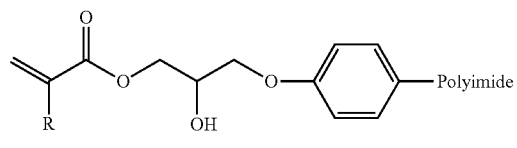
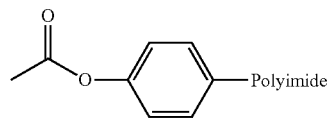  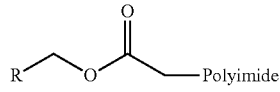
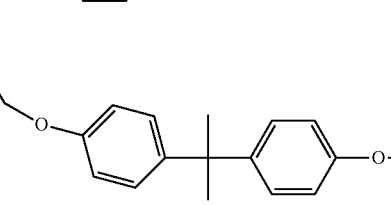 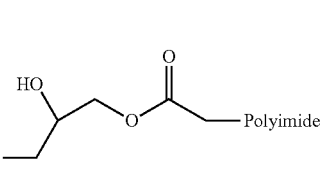 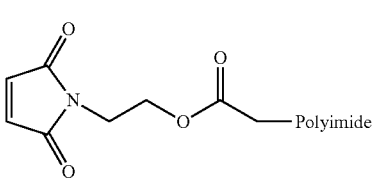
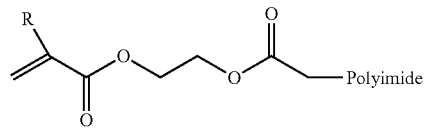 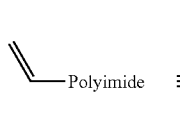 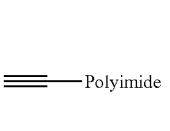 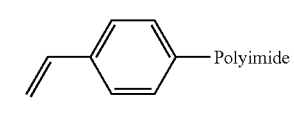

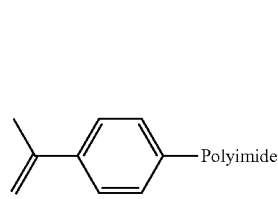

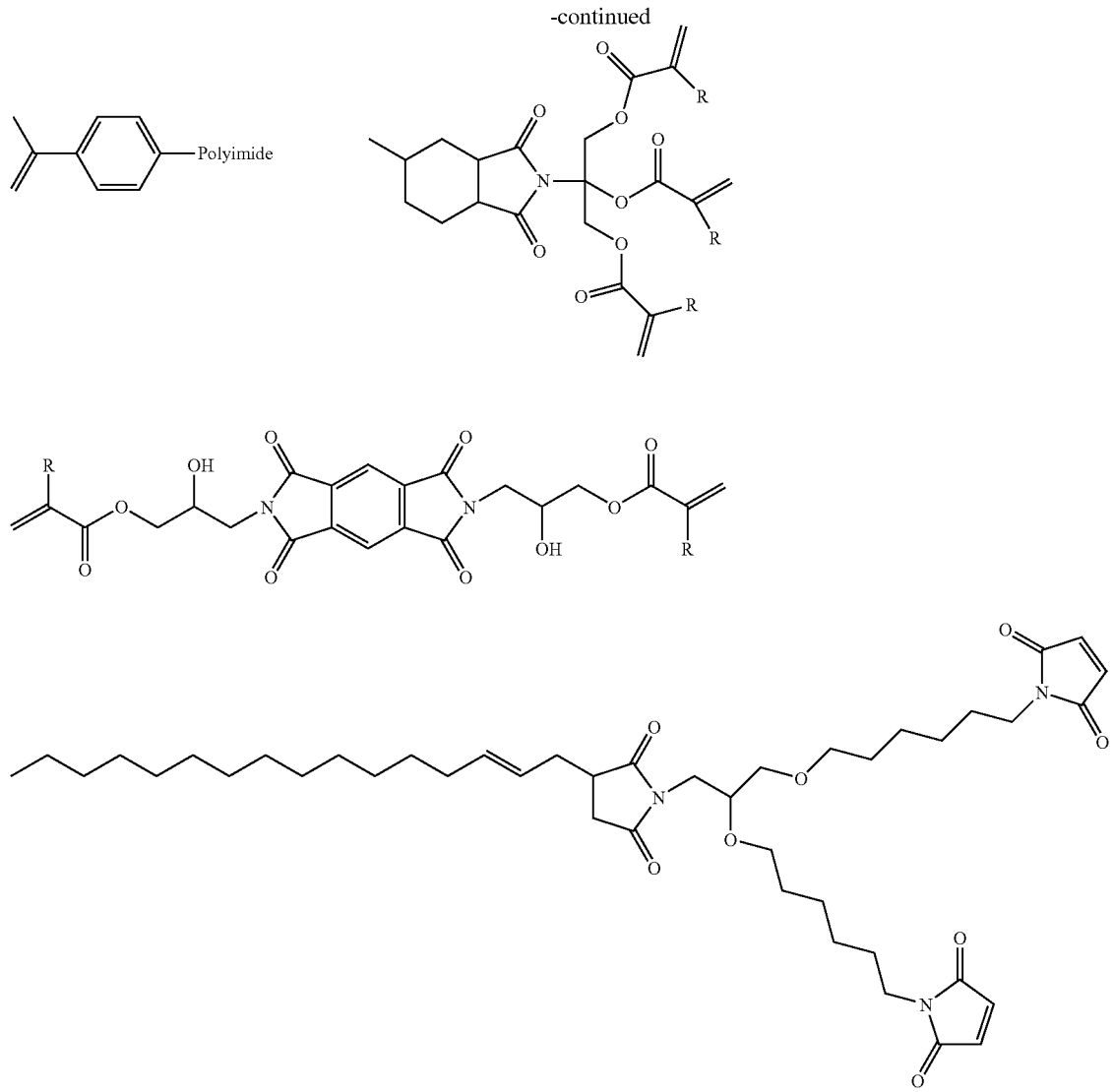

As set forth in the Examples herein, imide-extended maleimide compounds remain flexible at room temperature and are tougher than currently available maleimide-terminated rubbers. Thus, they may be used alone in adhesive compositions or added to available resins as a toughening agent. The maleimides of the invention will be present in the curable adhesive compositions in an amount from 0.05 to 98 weight percent (wt %) based on the organic components present (excluding any fillers).

In another embodiment, there are provided monomaleimides having the formula:

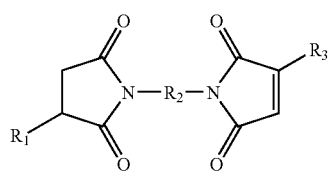

wherein: $R_1$ is substituted or unsubstituted aliphatic or alkenyl, or aromatic; and $R_2$ is substituted or unsubstituted aliphatic or alkenyl, aromatic, or siloxane; and $R_3$ is H or methyl.

In some embodiments, $R_1$ and $R_2$ are each independently substituted or unsubstituted linear, branched, or cyclic aliphatic or alkenyl moieties having from 2 to about 500 carbon atoms. In other embodiments, $R_1$ is a substituted or unsubstituted aromatic or heteroaromatic moiety having from 6 to about 14 carbon atoms.

In certain other embodiments, $R_2$ is a substituted or unsubstituted siloxane moiety having from 2 to about 1000 silicon atoms. In some embodiments, $R_2$ is a polysiloxane moiety, such as, for example, dimethylsiloxane, methylphenylsiloxane, diphenylsiloxane, or combinations thereof.

When $R_1$ and $R_2$ are substituted, the substituents present are those as set forth above.

In another embodiment of the invention, there are provided polymaleimides including polymers having a plurality of pendant repeating units having the structure:

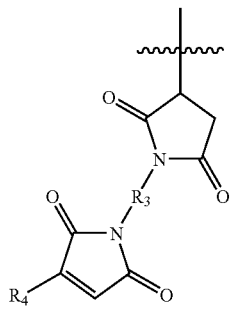

wherein: $R_3$ is substituted or unsubstituted aliphatic or alkenyl, aromatic, heteroaromatic, or siloxane moieties; and $R_4$ is H or methyl As used herein, the term "pendant" means that the structure set forth above is attached to a polymer main chain through at least one covalent bond.

In some embodiments, $R_3$ is a substituted or unsubstituted linear, branched, or cyclic aliphatic or alkenyl moiety having from 2 to about 500 carbon atoms. In other embodiments, $R_3$ is a substituted or unsubstituted aromatic or heteroaromatic moiety having from 6 to about 14 carbon atoms. In other embodiments, $R_3$ is a substituted or unsubstituted siloxane moiety having from 2 to about 1000 silicon atoms. $R_3$ can also be a polysiloxane, such as, for example, dimethylsiloxane, methylphenylsiloxane, diphenylsiloxane, or combinations thereof. When $R_3$ is substituted, the substituents are as set forth above.

In a further embodiment, there are provided polymaleimide polymers including a plurality of repeating units having the structure:

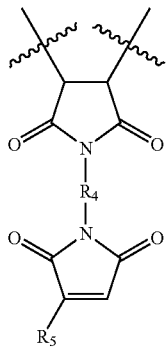

wherein: $R_4$ is a substituted or unsubstituted linear, branched, or cyclic aliphatic or alkenyl moiety having from 2 to about 500 carbon atoms, or an aromatic moiety; and $R_5$ is H or methyl In some embodiments, $R_4$ is a substituted or unsubstituted linear, branched, or cyclic aliphatic or alkenyl moiety having from 2 to about 500 carbon atoms. In other embodiments, $R_4$ is a substituted or unsubstituted aromatic or heteroaromatic moiety having from 6 to about 14 carbon atoms. In other embodiments, $R_4$ is a substituted or unsubstituted siloxane moiety having from 2 to about 1000 silicon atoms. $R_4$ can also be a polysiloxane, such as, for example, dimethylsiloxane, methylphenylsiloxane, diphenylsiloxane, methylhydrosiloxane, or combinations thereof. When $R_4$ is substituted, the substituents are as set forth above.

Examples of such polymaleimides are shown in FIG. 3. The precursor polymers or oligomers with pendant or main-chain succinic anhydride functional groups are known in the art. Examples of such materials include polyolefins (e.g., polyethylene, polypropylene, and the like) grafted with succinic anhydride residues, polybutadiene grafted with succinic anhydride residues, alternating or random copolymers of maleic anhydride with styrene or α-olefins, and the like. In order to prepare the polymaleimides of the invention, a large excess of diamine is typically used in order to suppress undesirable cross-linking reactions.

The imide-extended mono-, bis, and polymaleimides of the invention may be used independently in adhesive compositions, or may be combined with other adhesive compounds and resins. In one embodiment, the bismaleimide monomer of the invention may be used as the sole thermoset monomer of the adhesive composition. In another embodiment, the bismaleimide monomer of the invention may be with other thermoset monomers to make a fully formulated adhesive.

In one embodiment, there is provided an adhesive composition including an imide-extended bismaleimide compound and at least one curing initiator.

In some embodiments, the imide-extended bismaleimide compound is present in the composition from 0.05 weight percent to about 98 weight percent (wt %) based on total weight of the composition. In other embodiments, there is at least one co-monomer typically is present in the composition from 10 wt % to about 90 wt % based on total weight of the composition. Such comonomers include, for example, acrylates, methacrylates, maleimides, vinyl ethers, vinyl esters, styrenic compounds, allyl functional compounds, epoxy, oxetane, phenols, phenyl esters, and the like;

The at least one curing initiator is typically present in the composition from 0.1 wt % to about 5 wt % based on total weight of the composition, and is typically a free-radical initiator. As used herein, the term "free radical initiator" refers to any chemical species which, upon exposure to sufficient energy (e.g., light, heat, or the like), decomposes into two parts which are uncharged, but which each possess at least one unpaired electron. Preferred free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methylpropanenitrile), 2,2'-azobis(2-methylbutanenitrile), and 1,1'-azobis(cyclohexanecarbonitrile)), and the like.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In another embodiment of the invention, there are provided die-attach pastes including 0.05 weight percent to about 98 weight percent (wt %) of at least one imide-extended mono-, bis-, or polymaleimide compound described herein, or combinations thereof, based on total weight of the composition; optionally, 10 wt % to about 90 wt % of at least one co-monomer selected from the group consisting of acrylates, methacrylates, maleimides, vinyl ethers, vinyl esters, styrenic compounds, and allyl functional compounds, epoxies, oxetanes, phenols, phenyl esters, and the like, based on total weight of the composition; 0 to about 90 wt % of a filler; 0.1 wt % to about 5 wt % of at least one curing initiator, based on total weight of the composition; and 0.1 wt % to about 4 wt %, of at least one coupling agent, based on total weight of the composition.

In one embodiment, there is provided die-attach paste comprising:

a) 0.05 weight percent to about 98 weight percent (wt %) based on total weight of the composition, an imide-extended bismaleimide having the structure:

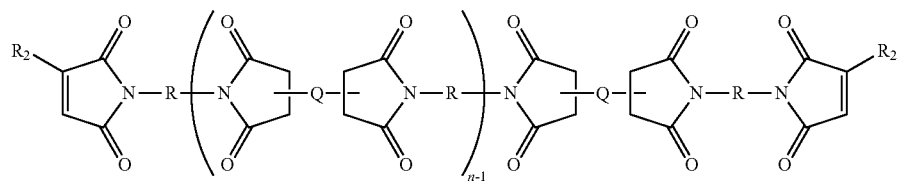

wherein:
R and Q are each independently substituted or unsubstituted aliphatic or alkenyl, aromatic, heteroaromatic, or siloxane moieties; $R_2$ is H or methyl; and
n is 1 to about 10, with the proviso that the imide-extended bismaleimide is not

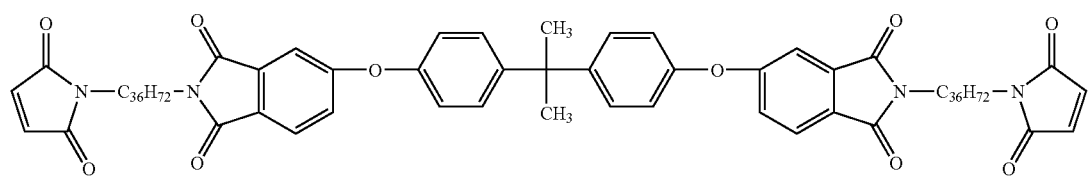

b) 0 to about 90 wt % of a filler;
d) 0.1 wt % to about 5 wt % of at least one curing initiator, based on total weight of the composition;
e) 0.1 wt % to about 4 wt %, of at least one coupling agent, based on total weight of the composition.

Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include silica, fumed silica, alumina, titania, and the like.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

In general, these compositions will cure within a temperature range of 80-360° C., and curing will be effected within a length of time of less than 1 minute to 120 minutes. As will be understood by those skilled in the art, the time and temperature curing profile for each adhesive composition will vary, and different compositions can be designed to provide the curing profile that will be suited to the particular industrial manufacturing process.

In certain embodiments, the adhesive compositions may contain compounds that lend additional flexibility and toughness to the resultant cured adhesive. Such compounds may be any thermoset or thermoplastic material having a Tg of 50° C. or less, and typically will be a polymeric material characterized by free rotation about the chemical bonds, the presence of ether groups, and the absence of ring structures. Suitable such modifiers include polyacrylates, poly(butadiene), poly-THF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of the maleimide and other monofunctional vinyl compound.

Inhibitors for free-radial cure may also be added to the adhesive compositions and die-attach pastes described herein to extend the useful shelf life of compositions containing the imide-extended maleimides. Examples of these inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants include derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis (3,5-di-tert-butyl-4-hydroxyhydrocinnamoyl)hydrazine; oxalylbis(benzylidenehydrazide); and N-phenyl-N'-(4-toluenesulfonyl)-p-phenylenediamine. Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

These compositions will perform within the commercially acceptable range for die attach adhesives. Commercially acceptable values for die shear for the adhesives on a 80×80 mil$^2$ silicon die are in the range of greater than or equal to 1 kg at room temperature, and greater than or equal to 0.5 kg at 260° C.

Advantageously, the imide-linked mono-, bis-, and poly-maleimide compounds and compositions of the present invention can be designed to remain as stable and flexible thermoplastic materials at room temperature. These thermoplastic imide-linked maleimides can be compounded with fillers, catalysts, inhibitors, and coupling agents to make a fully formulated adhesive package. Since the matrix of these compositions is thermoplastic, no settling will occur during shipping or storage. These characteristics therefore also permit packaging, shipment and storage without refrigeration. These properties also facilitate forming adhesives of the invention into various shapes and sizes for ease of use and application to electronic components and/or substrates. Thus, one aspect of the invention is a method for forming an adhesive rope that may be applied directly to a substrate for bonding electronic components thereto. According to this method, an imide-linked maleimide compound or adhesive composition is extruded in a rope shape. Unit lengths of the adhesive rope can then be dispensed into a packaging container. The length of adhesive rope dispensed can conveniently be selected by the desired use, application or unit of sale. Thus, a short rope of may be packaged for a single-use application while a longer length can be dispensed for bulk sale. In one embodiment of this method, the rope adhesive is a circular, square, or rectangular shape (across the short axis) of about two to 15 millimeters in diameter. The most preferred shape for the rope adhesive is where the material is extruded in the shape (in cross section) of a four lobbed clover or starfish. The invention also contemplates that other shapes may be manufactured by extrusion or molding, such as ribbons, dots, spheres, and the like. For example, the adhesive may be formed into single-use dots of suitable volume to bond a single electronic component to a substrate. Individual dots may be packaged on a disposable paper or film support and peeled off for use. The dot of adhesive may also be applied in advance to a suitable electronic device substrate (e.g. a lead frame, or ball grid array). Typically, the dots are in the range of 0.5 mm to 10 mm in diameter. A multiple number of dots may also be applied across the bond area of a substrate to accommodate larger devices. The dots may have the form of hemispherical or "Hershey's Kiss-like" shapes.

The present invention also provides methods for bonding an electronic component to a substrate using formed adhesive manufactures such as ropes, ribbons and dots. According to this method, the adhesive manufacture is dispensed directly onto the substrate in an amount sufficient to bond the desired electronic component. For example, a rope can be contacted with the substrate and the desired quantity can be cut from the end, thereby delivering a controlled amount of adhesive to the precise point of desired bonding. Optionally, the substrate can be heated to facilitate delivery of the adhesive by melting. When the amount of adhesive that will be required for a single application can be predetermined at the time of manufacture, individual aliquots of the adhesive can be premeasured, dispensed, and subsequently transferred to the substrate at the time of use, for example as individual dots. Once the adhesive is positioned onto the substrate, the electronic component is then contacted with the dispensed adhesive and the adhesive cured to bond the electronic component to the substrate. This method reduces waste, in that use of excess adhesive is avoided. Furthermore, this method facilitates precise positioning of adhesive and eliminates unwanted adhesive contamination of the substrate and surrounding work area. The thermoplastic nature of these adhesives offers other significant advantages for commercial applications compared to the traditional paste adhesives used for die attach. The materials described here don't require the −40° C. refrigerated storage conditions traditionally used for the paste adhesives. A fully formulated thermoplastic adhesive mixture that contains sufficient inhibitors can be kept for several months at or just below room temperature without any loss of performance. The thermoplastic nature of this adhesive furthermore prevents any settling of the filler from the resin matrix during such storage.

Conveniently, the adhesive compositions of the invention can be packaged into kits for consumption by the end-user. Included in each kit is a package containing a sufficient amount of a curable imide-linked maleimide adhesive composition to bond at least one electronic component to a substrate and instructions for using said adhesive to bond an electronic component to a substrate. The adhesive supplied in the kit may be, for example, in bulk, rope or dot form, depending of the intended end-use. The instructions are contemplated to include directions for preparation of the elements that will be bonded (e.g., electronic components and substrates) application of the adhesive, suggested quantities for various applications, and conditions required to cure the adhesive. The kit format will be particularly useful for maleimide adhesives of the invention with characteristics that may not be well known in the art. For example, techniques for application and curing of adhesive manufactures (e.g., ropes and dots) can be described and illustrated.

Additional embodiments of the invention include adhesive bonded structures containing curable imide-linked maleimide adhesive compositions. Nonlimiting examples of the adhesive bonded structures include electronic components bonded to a substrate, and circuit components bonded to printed wire boards.

In yet another embodiment of the invention, there are provided assemblies of components adhered together employing the above-described adhesive compositions and/or die attach pastes. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like.

Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In accordance with still another embodiment of the present invention, there are provided methods for adhesively attaching two component parts to produce the above-described assemblies. Thus, for example, a first article can be adhesively attached to a second article, employing a method including:
(a) applying the above-described adhesive composition to the first article,
(b) bringing the first and second article into intimate contact to form an assembly wherein the first article and the second article are separated only by the adhesive composition applied in (a), and thereafter,
(c) subjecting the assembly to conditions suitable to cure the adhesive composition.

Similarly, a microelectronic device can be adhesively attached to a substrate, employing a method comprising:
(a) applying the above-described die attach paste to the substrate and/or the microelectronic device,
(b) bringing the substrate and the device into intimate contact to form an assembly wherein the substrate and the device are separated only by the die attach composition applied in (a), and thereafter,
(c) subjecting the assembly to conditions suitable to cure the die attach composition.

Conditions suitable to cure invention die attach pastes include subjecting the above-described assembly to a temperature of less than about 400° C. for about 0.5 up to 2 minutes. This rapid, short duration heating can be accomplished in a variety of ways, e.g., with an in-line heated rail, a belt furnace, or the like. Optionally, the material can be oven cured at 80-400° C.

In still another embodiment of the invention, there is provided a method for producing an imide-extended bismaleimide monomer. Such a method can be performed, for example, by contacting a dianhydride with a diamine under conditions suitable to form an imide having terminal amino moieties; and contacting the terminal amino moieties with maleic anhydride under conditions suitable to form a maleimide, thereby producing an imide-extended bismaleimide monomer.

It is understood that using the compounds and methods of the present invention, it is possible to prepare adhesives having a wide range of cross-link density by the judicious choice and amount of mono-, bis- or polyfunctional compounds. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

"Cross-linking," as used herein, refers to the attachment of two or more polymer chains by bridges of an element, a molecular group, or a compound. In general, crosslinking of the compounds of the invention takes place upon heating. As cross-linking density is increased, the properties of a material can be changed from thermoplastic to thermosetting.

The following examples are intended only to illustrate the present invention and should in no way be construed as limiting the subject invention.

EXAMPLES

The Synthesis of Imide-Extended Mono-, Bis-, and Polymaleimides

Example 1

A 500 ml round bottom flask equipped with a Teflon coated stir bar was charged with 250 ml of toluene. Triethylamine, 35 g (0.35 mole) was added to the flask, followed by the slow addition of 35 g (0.36 mole) of anhydrous methanesulphonic acid to form a salt. The mixture was allowed to stir for approximately 10 minutes, followed by the addition of 57 g (0.11 mole) of Versamine 552 (dimer diamine, Cognis Corporation). Pyromellitic dianhydride (10.9 g, 0.05 mole) was slowly added to the stirred mixture. A Dean-Stark trap and condenser were attached to the flask, and the mixture was heated to reflux for 2 hours to form an amine-terminated diimide. The theoretical quantity of water from this condensation had been collected by this time. The reaction mixture was cooled down to room temperature and 12.8 g (0.13 mole) of maleic anhydride was added to the flask, followed by the of 5 g of anhydrous methanesulphonic acid. The mixture was brought to reflux for an additional 12 hours to obtain the expected amount of water. An additional 100 ml of toluene was added to the flask after it had been cooled down to room temperature, and the mixture was then allowed to settle. The solution was decanted, and the salt was rinsed with additional toluene (2×100 ml). The extracts were combined and then again allowed to settle overnight in order to provide sufficient time for additional salt and acid to separate. The solution was filtered through a glass-fritted funnel tightly packed with 30 g of silica gel. The solvent was removed under vacuum to produce 60 g (84% yield) of a dark waxy resin.

Example 2

Similar to the method outlined in the previous example, a salt was formed by mixing 38 g (0.38 mole) of triethylamine with 38 g (0.39 mole) of anhydrous methanesulphonic acid in 250 ml of toluene. Versamine 552, 59 g (0.11 mole) was added to the flask, followed by the slow addition of 16.1 g (0.05 mole) of 3,3',4,4'-benzophenone tetracarboxylic dianhydride. About two of hours of reflux were required for the azeotropic removal of the water to form the amine-terminated diimide. The mixture was cooled down to room temperature, followed by the addition of 12.5 g (0.13 mole) of maleic anhydride and 5 g of methanesulphonic acid. The mixture was refluxed again for 12 hours to form the bismaleimide. The product was worked-up according to the procedure described in the previous example. A dark amber colored resin (65 g, 82% yield) was collected after the complete removal of the solvent.

Example 3

A salt was made by mixing 10 g (0.10 mole) of triethylamine with 11 g (0.11 mole) of methanesulphonic acid in 200 ml of toluene. Verasmine 552, 32 g (0.06 mole) was added to the mixture, followed by the slow addition of 13.5 g (0.03 mole) of 1,1,3,3-tetramethyl-1,3-bis(norbornyldicarboxylic anhydride)disiloxane. The amine-terminated diimide was formed after the azeotropic distillation of the water, which required approximately 1 hour of reflux. The mixture was cooled down, followed by the addition of 10 g (0.10 mole) of maleic anhydride along with 3 g of methanesulphonic acid. The mixture was refluxed for 18 hours to collect the required amount of water in the Dean-Stark trap. The work-up of the product was conducted as outlined in the previous examples. The final material (35 g, 73% yield) was obtained as a dark-amber colored resin after the removal of the solvent.

Example 4

A salt was prepared by mixing 40 g (0.40 mole) triethylamine with 40 g (0.42 mole) methanesulphonic acid in 200 ml of toluene. This was followed by the sequential addition of 57 g (0.11 mol) of Versamine 552 and 17 g (0.05 mole) of 2,8-decadiene-1,10-disuccinic anhydride. The mixture was refluxed for 12 hours with azeotropic removal of the water to produce the amine-terminated diimide. The mixture was then cooled down to room temperature and 12.8 g (0.13 mol) of maleic anhydride and 5 g. of methanesulphonic acid were then added to the flask. The mixture was again heated to reflux overnight with azeotropic removal of the water. Work-up of the product gave 65 g (82% yield) of an amber-colored resin.

Example 5

A salt was formed by mixing 35 g. (0.35 mole) of triethylamine with 36 g. (0.37 mole) of methanesulphonic acid in 250 ml of toluene (inside a 500 ml flask). Verasmine 552, 90 g (0.17 mole) was added to the flask, followed by the slow addition of 24 g. (0.11 mole) of pyromellitic dianhydride. About two of hours of reflux were required for the complete azeotropic removal of the water to form the amine terminated diimide. The mixture was then cooled down to room temperature and 13 g (0.13 mole) of maleic anhydride and 10 g of methanesulphonic acid were then added. The mixture was refluxed again for 12 hours to form the imide-linked bismaleimide. The product was worked up according to the procedure described in the previous example. A dark amber colored resin (100 g, 82% yield) was collected after the complete removal of the solvent.

Example 6

A salt was formed by mixing 50 g (0.50 mole) of triethylamine with 50 g (0.52 mole) of anhydrous methanesulphonic acid in 400 mL of toluene (inside a one liter flask). Bis (aminomethyl)tricyclo[5.2.1.2,6]decane, 33 g. (0.17 mole) was added to the flask, followed by the slow addition of 42 g (0.08 mole) 4,4'-bisphenol-A dianhydride. A couple of hours of reflux were required for the azeotropic removal of the water to form the amine-terminated diimide. The mixture was cooled down to room temperature, followed by the addition of 22 g (0.22 mole) of maleic anhydride and 8 g of methanesulphonic acid. The mixture was refluxed again for 16 hours to form the imide-linked bismaleimide. The product was worked up according to the procedure described in the previous example. The solvent was removed to obtain 80 g (94% yield) of a glassy, light yellow, solid.

Example 7

A salt was formed by mixing 35 g (0.35 mole) of triethylamine with 36 g (0.38 mole) of anhydrous methanesulphonic acid in 400 ml of toluene (inside a 1000 ml flask). Forty-two grams (0.10 mole) of 2,2'-Bis[4-(4-aminophenoxy)phenyl] propane was added to the flask, followed by the slow addition of 11 g (0.05 mole) of pyromellitic dianhydride. About two hours of reflux were required for the azeotropic removal of the water to form the desired amine-terminated diimide. The mixture was cooled down to room temperature, followed by the addition of 8 g (0.08 mole) of maleic anhydride and 8 g of methanesulphonic acid. The mixture was refluxed again for 6 hours to form the bismaleimide. The work-up of the product consisted of removal of the solvent under vacuum, followed by washing the solid on a Buchner funnel with water to remove the salt and acid. A final rinse with acetone was used to remove most of the water. The product was laid out in a shallow pan and dried in a oven overnight at approximately 100° C. A fine yellow powder (44 g, 86% yield) was obtained after drying.

Example 8

A salt was formed by mixing 35 g (0.35 mole) of triethylamine with 36 g (0.38 mole) of anhydrous methanesulphonic acid and 400 ml of toluene (inside a 1000 ml round-bottom flask). Bisphenol-A dianhydride (32 g, 0.06 mole) of was then added to the flask, followed by the addition of 16 g. (0.03 mole) of Versamine 552. The mixture was stirred at room temperature for an hour, followed by the addition of 24 g (0.06 mole) of 2,2'-Bis[4-(4-aminophenoxy)phenyl]propane to the flask. Azeotropic removal of the water was conducted over approximately 20 hours to form the desired amine-terminated imide. The mixture was then cooled down to room temperature, followed by the addition of 10 g (0.10 mol) of maleic anhydride and 5 g of methanesulphonic acid. The mixture was refluxed again for 18 hours to form the imide-extended bismaleimide. The product was worked up according to the procedure described in the previous example. After removal of the solvent, 60 g (82% yield) of a yellow, friable, glassy solid was obtained.

Example 9

A 500 ml round bottom flask equipped with a teflon coated stir bar was charged with 24 g (0.40 mole) of ethylenediamine along with 100 ml of toluene. This was followed by the slow addition of 100 g of polybutadiene grafted with 8% by weight maleic anhydride (RI130MA8, Sartomer). The azeotropic removal of the water and excess ethylenediamine was conducted over a twelve hour reflux period. The removal of the excess ethylene diamine was aided by the addition of steam into the reaction vessel. The salt (25 g) of triethylaminemethanesulphonic acid was then added to the solution, along with an additional 3 g of methanesulphonic acid and 12 g (0.12 mole) of maleic anhydride. The azeotropic removal of the water was conducted over 12 hours to form the polymaleimide. The work-up of the product was conducted according to the previous examples to obtain 100 g of an amber colored viscous liquid resin.

Example 10

Toluene (350 ml) was added to a one liter round bottom flask equipped with a Teflon coated stir bar. Triethylamine, 50 g (~0.50 mole) was added to the flask followed by the slow addition of 50 g (0.52 mole) of anhydrous methanesulphonic acid. The mixture was allowed to stir at room temperature approximately 10 minutes, followed by the addition of 90 g (0.17 mole) of Versamine 552 (dimer diamine, Cognis Corporation). To the mixture was added 41 g (0.08 mole) of BPADA (4,4'-bisphenol-A dianhydride, GE Plastics). A Dean-Stark trap and condenser were attached to the flask, and the mixture was heated to reflux. After approximately two hours the expected amount of water was collected corresponding to the complete conversion to the amine terminated diimide. The mixture was allowed to cool down to below 40° C., and 22 g (0.23 mole, ~20% excess) of crushed maleic anhydride was added to the flask, followed by the addition of an extra 10 g of anhydrous methanesulphonic acid. The mixture was again slowly heated to reflux. Approximately 18 hours of reflux were required to collect the expected amount of water in the Dean-Stark trap. After cooling down to room temperature an extra 200 ml of toluene was added to the flask; the stirring was stopped at this point and the mixture was allowed to separate. The upper (toluene solution) fraction was carefully decanted into a 2 liter Erlenmeyer flask. The salt was washed with toluene (2×500 ml) the rinses were also decanted and combined. The amber solution was allowed to settle overnight to allow sufficient time for more salt and acid to separate from the combined toluene solution. The solution was then filtered through a glass-fritted funnel tightly packed with 65 g of silica gel. Following filtration the silica gel was washed with an extra 100 ml of toluene. The toluene was removed under reduced pressure to provide 120 g (~85% yield) of a dark amber colored resin.

Example 11

Tensile adhesion testing was done on some of the products from the preceding examples. The only component added to the test resin was 2% by weight of dicumyl peroxide initiator. The catalyzed resin mix was then used to affix aluminum studs to copper slugs. The aluminum posts had a contact head diameter of 290 mils. The copper slugs had dimensions of 1000×400×150 mils. Ten of these test assemblies were constructed for each of the catalyzed resin mixtures. The parts were cured for thirty minutes in an oven at 200° C. The parts were then allowed to cool to room temperature and the adhesive strength was determined using a Sebastian III tensile tester. A control composition was also run along side the test mixtures. The control mix used was the bismaleimide derived from the dimer diamine (i.e. Versamine 552) also catalyzed with 2% dicumyl peroxide.

TABLE 1

Tensile Adhesion Test Results

| | Stud Pull Value (pounds force) | |
|---|---|---|
| Part | Example 10 | Control |
| 1 | 66 | 23 |
| 2 | 54 | 16 |
| 3 | 57 | 15 |
| 4 | 75 | 12 |
| 5 | 47 | 19 |
| 6 | 71 | 9 |
| 7 | 52 | 22 |
| 8 | 70 | 18 |
| 9 | 63 | 8 |
| 10 | 77 | 6 |
| Average | 63 | 15 |
| $F_{n-1}$ | 10 | 6 |

TABLE 2

Tensile Adhesion Test Results

| | Stud Pull Value (pounds force) | | | |
|---|---|---|---|---|
| Part | Example 1 | Example 2 | Example 5 | Control |
| 1 | 73 | 97 | 95 | 30 |
| 2 | 59 | 69 | 145 | 15 |
| 3 | 91 | 68 | 103 | 23 |
| 4 | 96 | 77 | 113 | 7 |
| 5 | 98 | 88 | 143 | 21 |
| 6 | 97 | 79 | 156 | 16 |
| 7 | 102 | 81 | 127 | 28 |
| 8 | 60 | 93 | 126 | 24 |
| 9 | 101 | 81 | 113 | 25 |
| 10 | 61 | 71 | 126 | 25 |
| Average | 84 | 80 | 125 | 21 |
| $F_{n-1}$ | 18 | 9.9 | 19 | 6.9 |

The adhesion results for all of the examples shown in Tables 1 and 2 were clearly superior to the control test composition. While not wishing to be bound by theory, it is believed that the improvement seen here is a direct result of the reduced cross-link density and/or reduced cure shrinkage of the invention composition versus the BMI derived solely from the dimer diamine.

While this invention has been described with respect to these specific examples, it should be clear that other modifications and variations would be possible without departing from the spirit of this invention.

What is claimed is:

1. A polymer comprising:
   (a) the main polymeric chain; and
   (b) a plurality of the units having the structure I pendant from the main polymeric chain:

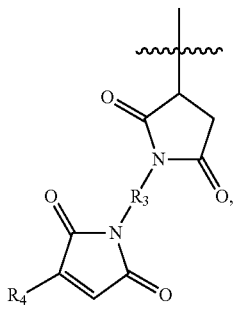

wherein
the symbol "~~~~" signifies the main polymeric chain;
$R_3$ is selected from the group consisting of a substituted or an unsubstituted aliphatic or alkenyl moiety having between 2 and about 500 carbon atoms, an aromatic, a heteroaromatic, and a siloxane moieties; and
$R_4$ is selected from the group consisting of H and methyl.

2. The polymer of claim 1, wherein $R_3$ is a substituted or an unsubstituted linear, branched, or cyclic aliphatic or alkenyl moiety having between 2 and about 500 carbon atoms.

3. The polymer of claim 1, wherein $R_3$ is a substituted or an unsubstituted aromatic or heteroaromatic moiety having between 6 and 20 carbon atoms.

4. The polymer of claim 1, wherein $R_3$ is a substituted or an unsubstituted siloxane moiety having between 2 and about 1000 silicon atoms.

5. The polymer of claim 4, wherein the siloxane moiety is a polysiloxane.

6. The polymer of claim 5, wherein the polysiloxane comprises repeating units selected from the group consisting of dimethylsiloxane, methylphenylsiloxane, diphenylsiloxane, methylhydrosiloxane, and combinations thereof.

7. The polymer of claim 1, wherein the substituted aliphatic, aromatic, heteroaromatic, or siloxane moieties comprise substituents selected from the group consisting of an alkyl, an alkenyl, an alkynyl, hydroxy, oxo, an alkoxy, mercapto, a cycloalkyl, a substituted cycloalkyl, a heterocyclic, a substituted heterocyclic, an aryl, a substituted aryl, a heteroaryl, a substituted heteroaryl, an aryloxy, a substituted aryloxy, a halogen, a haloalkyl, cyano, nitro, nitrone, an amino, an amido, —C(O)H, —C(O)—, —S—, —S(O)$_2$—, —OC(O)—O—, —NR—C(O)—, —NR—C(O)—NR—, and —OC(O)—NR—, wherein R is selected from the group consisting of H, a lower alkyl, an acyl, an oxyacyl, carboxyl, carbamate, sulfonyl, a sulfonamide, and sulfuryl.

8. The polymer of claim 1, wherein the main polymer chain is formed by a polymer selected from the group consisting of polyolefins.

9. An adhesive composition comprising at least one polymer of claim 1 and at least one curing initiator.

10. The adhesive composition of claim 9 comprising:
a) 0.05 weight percent to about 98 weight percent (wt %) of polymaleimide polymer, based on total weight of the composition;
b) 0 to about 90 wt % of a filler;
d) 0.1 wt % to about 5 wt % of at least one curing initiator, based on total weight of the composition;
e) 0.1 wt % to about 4 wt %, of at least one coupling agent, based on total weight of the composition, wherein the adhesive composition is a die attach paste.

11. The adhesive composition of claim 10, wherein the coupling agent is a silicate ester, a metal acrylate salt, zirconate, or a titanate, or the filler is silica, or the at least one curing initiator is a peroxide.

12. An assembly comprising a first article permanently adhered to a second article by a cured aliquot of the adhesive composition of claim 10.

13. A kit for bonding an electronic component to a substrate comprising a package containing an amount of an adhesive composition of claim 9 sufficient to bond at least one electronic component to a substrate; and
instructions for using the adhesive composition to bond the electronic component to the substrate.

14. A polymaleimide polymer comprising a plurality of repeating units having the structure:

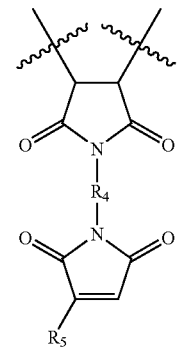

wherein: $R_4$ is substituted or unsubstituted aliphatic, alkenyl moiety having from 2 to about 500 carbon atoms, aromatic, heteroaromatic, or siloxane moieties and $R_5$ is H or methyl.

15. The polymer of claim 14, wherein $R_4$ is a substituted or unsubstituted linear, branched, or cyclic aliphatic or alkenyl moiety having from 2 to about 500 carbon atoms.

16. The polymer of claim 14, wherein $R_4$ is a substituted or unsubstituted aromatic or heteroaromatic moiety having from 6 to about 20 carbon atoms.

17. The polymer of claim 14, wherein $R_4$ is a substituted or unsubstituted siloxane moiety having from 2 to about 1000 silicon atoms.

18. The polymer of claim 17, wherein the siloxane moiety is a polysiloxane.

19. The polymer of claim 18, wherein the polysiloxane comprises repeating units selected from dimethylsiloxane, methylphenylsiloxane, diphenylsiloxane, methylhydrosiloxane, or combinations thereof.

20. The polymer of claim 14, wherein substituted aliphatic, aromatic, heteroaromatic, or siloxane moieties comprise substituents selected from alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O) —, —S—, —S(O)$_2$—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, or sulfuryl.

21. An adhesive composition comprising at least one polymaleimide polymer of claim 14 and at least one curing initiator.

* * * * *